United States Patent [19]
Schwan

[11] 3,991,075
[45] Nov. 9, 1976

[54] 1-[3-(4-HYDROXYBENZYLAMINO)-PROPYL]PYRROLIDINE DIHYDROBROMIDE AND INTERMEDIATE THEREFOR

[75] Inventor: Thomas J. Schwan, Norwich, N.Y.

[73] Assignee: Morton-Norwich Products, Inc., Norwich, N.Y.

[22] Filed: May 12, 1975

[21] Appl. No.: 576,346

[52] U.S. Cl. .................. 260/326.5 L; 260/326.85; 424/274
[51] Int. Cl.² ...................................... C07D 207/06
[58] Field of Search ............................ 260/326.5 L

[56] References Cited
UNITED STATES PATENTS
3,308,133  3/1967  Van der Burg ............. 260/326.5 X Primary Examiner—Nicholas S. Rizzo
Assistant Examiner—Mary C. Vaughn
Attorney, Agent, or Firm—Anthony J. Franze

[57] ABSTRACT

A compound 1-[3-(4 hydroxybenzylamino)propyl]pyrrolidine dihydrobromide possesses pharmacological activity as an antihypertensive agent.

2 Claims, No Drawings

1-[3-(4-HYDROXYBENZYLAMINO)PROPYL]PYRROLIDINE DIHYDROBROMIDE AND INTERMEDIATE THEREFOR

This invention relates to chemical compounds. In particular it is concerned with a compound of the formula:

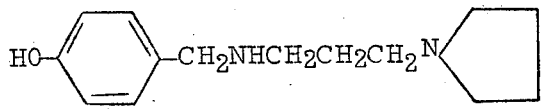

When administered subcutaneously or orally to animals this compound exhibits antihypertensive activity. Administration of 100 mg/kg/day of this compound to rats for seven days caused marked inhibition of the responses to norephrinephrine, renin and angiotensin.

Moreover, the hydrochloride salt of chemical intermediate for this compound, 1-[3-(4-methoxybenzylamino)propyl]pyrrolidine, also exhibits antihypertensive activity. The salt can be readily converted to the free base by treatment with base.

In order that this invention be readily available to and understood by those skilled in the art the following illustrative examples are supplied:

EXAMPLE I

1-[3-(4-Methoxybenzylamino)-1-propyl]pyrrolidine Dihydrochloride

A solution of p-anisaldehyde (68 g., 0.5 mole) and 1-(3-aminopropyl)pyrrolidine (64 g., 0.5 mole) in methanol (400 ml) was treated slowly with sodium borohydride (19 g., 0.5 mole) at 15°–25°. When the addition was completed the reaction mixture was stirred for 1 hour and then the solvent was removed in vacuo. The resulting residue was treated with water (500 ml) and then extracted with ether (2 × 250 ml). The combined ether extracts were dried over magnesium sulfate and then concentrated in vacuo to give 124 g. (100%) of the free base. The dihydrochloride was prepared by dissolving the free base in methanol and adding methanolic hydrogen chloride followed by removal of the methanol in vacuo. An analytical sample, m.p. 188°–189°, was obtained by recrystallization from acetonitrile.

Anal. Calcd. for $C_{15}H_{24}N_2O.2HCl$: C, 56.07; H, 8.16; N, 8.72. Found: C, 55.84; H, 8.13; N, 8.64.

EXAMPLE II

1-[3-(4-Hydroxybenzylamino)-1-propyl]pyrrolidine Dihydrobromide

A 500 ml flask was charged with I, free base, (74 g. 0.3 mole) and hydrobromic acid (48%, 250 ml). The reaction mixture was refluxed for 6 hours, and then concentrated to give 95 g. (80%) of title product. The analytical sample, m.p. 203°–205°, was obtained by two recrystallizations from ethanol.

Anal. Calcd. for $C_{14}H_{22}N_2O.2HBr$: C, 42.44; H, 6.11; N, 7.07. Found: C, 42.58; H, 6.04; N, 6.94.

What is claimed is:

1. The compound of the formula:

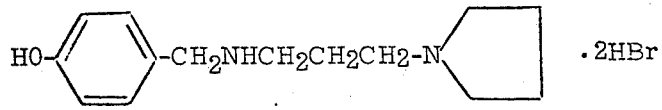

2. The compound 1-[3-(4-methoxybenzylamino)propyl]pyrrolidine dihydrochloride.